(12) United States Patent
Stroumpoulis

(10) Patent No.: US 8,678,993 B2
(45) Date of Patent: Mar. 25, 2014

(54) REMOTELY ADJUSTABLE GASTRIC BANDING SYSTEM

(75) Inventor: Dimitrios Stroumpoulis, Goleta, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 937 days.

(21) Appl. No.: 12/705,343

(22) Filed: Feb. 12, 2010

(65) Prior Publication Data

US 2011/0201875 A1 Aug. 18, 2011

(51) Int. Cl.
*A61B 17/00* (2006.01)
(52) U.S. Cl.
USPC ............................................. 600/37
(58) Field of Classification Search
USPC ............... 600/29–31, 37; 417/53–55; 606/151–158
See application file for complete search history.

(56) References Cited

U.S. PATENT DOCUMENTS

| | | | |
|---|---|---|---|
| 2,163,048 A | 6/1939 | McKee | |
| 3,667,081 A | 6/1972 | Burger | |
| 3,840,018 A | 10/1974 | Heifetz | |
| 4,118,805 A | 10/1978 | Reimels | |
| 4,157,713 A | 6/1979 | Clarey | |
| 4,340,083 A | 7/1982 | Cummins | |
| 4,406,656 A | 9/1983 | Hattler et al. | |
| 4,450,375 A | 5/1984 | Siegal | |
| 4,592,339 A | 6/1986 | Kuzmak | |
| 4,592,355 A | 6/1986 | Antebi | |
| 4,601,713 A | 7/1986 | Fuqua | |
| 4,671,351 A | 6/1987 | Rappe | |
| 4,696,288 A | 9/1987 | Kuzmak | |
| 4,760,837 A | 8/1988 | Petit | |
| 4,881,939 A | 11/1989 | Newman | |
| 4,883,467 A | 11/1989 | Franetzki | |
| 4,944,659 A | 7/1990 | Labbe | |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Corno et al.; "A new implantable device for telemetric control of pulmonary blood flow," New Ideas; received Apr. 24, 2004; received in revised form Jul. 12, 2002; accepted Jul. 22, 2002.

(Continued)

*Primary Examiner* — Charles A Marmor, II
*Assistant Examiner* — Catherine E Burk
(74) *Attorney, Agent, or Firm* — Gordon & Jacobson, PC

(57) ABSTRACT

An implantable device comprises a reservoir that contains a fluid for filling an inflatable portion of a gastric band. A device is coupled to the reservoir and includes stored potential energy having a first state and a second state. The first state represents a higher level of potential energy and the second state represents a lower level of potential energy. The implantable device further comprises a filling valve coupled between the reservoir and the gastric band, and the filling valve is configured to be opened in response to a first telemetric signal. The stored potential energy decreases from the first state to the second state when the filling valve is open, and a filling amount of the fluid moves from the reservoir to the gastric band when the stored potential energy decreases from the first state to the second state.

7 Claims, 8 Drawing Sheets

(56) References Cited

U.S. PATENT DOCUMENTS

| | | |
|---|---|---|
| 5,045,060 A | 9/1991 | Melsky et al. |
| 5,074,868 A | 12/1991 | Kuzmak |
| 5,089,019 A | 2/1992 | Grandjean |
| 5,120,313 A | 6/1992 | Elftman |
| 5,160,338 A | 11/1992 | Vincent |
| 5,226,429 A | 7/1993 | Kuzmak |
| 5,259,399 A | 11/1993 | Brown |
| 5,326,349 A | 7/1994 | Baraff |
| 5,343,894 A | 9/1994 | Frisch et al. |
| 5,360,445 A | 11/1994 | Goldowsky |
| 5,449,368 A | 9/1995 | Kuzmak |
| 5,458,568 A | 10/1995 | Racchini et al. |
| 5,496,312 A | 3/1996 | Klicek |
| 5,535,752 A | 7/1996 | Halperin |
| 5,554,113 A | 9/1996 | Novak |
| 5,562,714 A | 10/1996 | Grevious |
| 5,601,604 A | 2/1997 | Vincent |
| 5,658,298 A | 8/1997 | Vincent et al. |
| 5,676,162 A | 10/1997 | Larson, Jr. |
| 5,733,257 A | 3/1998 | Sternby |
| 5,748,200 A | 5/1998 | Funahashi |
| 5,759,015 A | 6/1998 | Van Lintel et al. |
| 5,766,232 A | 6/1998 | Grevious |
| 5,807,311 A | 9/1998 | Palestrant |
| 5,861,014 A | 1/1999 | Familoni |
| RE36,176 E | 3/1999 | Kuzmak |
| 5,910,149 A | 6/1999 | Kuzmak |
| 5,938,669 A * | 8/1999 | Klaiber et al. ............ 606/157 |
| 6,024,340 A | 2/2000 | Lazarus et al. |
| 6,024,704 A | 2/2000 | Meador |
| 6,042,345 A | 3/2000 | Bishop et al. |
| 6,067,991 A | 5/2000 | Forsell |
| 6,074,341 A | 6/2000 | Anderson et al. |
| 6,083,249 A | 7/2000 | Familoni |
| 6,102,922 A | 8/2000 | Jakobsson et al. |
| 6,164,933 A | 12/2000 | Tani et al. |
| 6,210,347 B1 | 4/2001 | Forsell |
| 6,221,024 B1 | 4/2001 | Miesel |
| 6,306,088 B1 | 10/2001 | Krausman et al. |
| 6,327,503 B1 | 12/2001 | Familoni |
| 6,417,750 B1 | 7/2002 | Sohn |
| 6,432,040 B1 | 8/2002 | Meah |
| 6,439,539 B1 | 8/2002 | Powell |
| 6,450,173 B1 | 9/2002 | Forsell |
| 6,450,946 B1 | 9/2002 | Forsell |
| 6,450,987 B1 | 9/2002 | Kramer |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,475,136 B1 | 11/2002 | Forsell |
| 6,511,490 B2 | 1/2003 | Robert |
| 6,527,701 B1 | 3/2003 | Sayet et al. |
| 6,547,801 B1 | 4/2003 | Dargent et al. |
| 6,579,301 B1 | 6/2003 | Bales et al. |
| 6,676,674 B1 | 1/2004 | Dudai |
| 6,681,135 B1 | 1/2004 | Davis et al. |
| 6,685,668 B1 | 2/2004 | Cho et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel |
| 6,811,136 B2 | 11/2004 | Eberhardt et al. |
| 6,820,651 B2 | 11/2004 | Seuret et al. |
| 6,834,201 B2 | 12/2004 | Gillies |
| 6,871,090 B1 | 3/2005 | He |
| 6,889,086 B2 | 5/2005 | Mass et al. |
| 6,940,467 B2 | 9/2005 | Fischer |
| 6,966,875 B1 | 11/2005 | Longobardi |
| 7,017,583 B2 | 3/2006 | Forsell |
| 7,017,883 B2 | 3/2006 | Bayer et al. |
| 7,021,147 B1 | 4/2006 | Subramanian |
| 7,037,344 B2 | 5/2006 | Kagan et al. |
| 7,040,349 B2 | 5/2006 | Moler et al. |
| 7,048,519 B2 | 5/2006 | Fong et al. |
| 7,058,434 B2 | 6/2006 | Wang |
| 7,060,080 B2 | 6/2006 | Bachmann |
| 7,066,486 B2 | 6/2006 | Lee |
| 7,118,526 B2 | 10/2006 | Egle |
| 7,128,750 B1 | 10/2006 | Stergiopulos |
| 7,191,007 B2 | 3/2007 | Desai |
| 7,198,250 B2 | 4/2007 | East |
| 7,204,821 B1 | 4/2007 | Clare et al. |
| 7,206,637 B2 | 4/2007 | Salo |
| 7,238,191 B2 | 7/2007 | Bachmann |
| 7,282,023 B2 | 10/2007 | Frering |
| 7,284,966 B2 | 10/2007 | Xu et al. |
| 7,288,064 B2 | 10/2007 | Boustani et al. |
| 7,310,557 B2 | 12/2007 | Maschino et al. |
| 7,311,503 B2 | 12/2007 | Van Lintel et al. |
| 7,311,716 B2 | 12/2007 | Byrum |
| 7,311,717 B2 | 12/2007 | Egle |
| 7,314,443 B2 | 1/2008 | Jordan et al. |
| 7,338,433 B2 | 3/2008 | Coe |
| 7,351,198 B2 | 4/2008 | Byrum |
| 7,351,240 B2 | 4/2008 | Hassler |
| 7,353,747 B2 | 4/2008 | Swayze et al. |
| 7,364,542 B2 | 4/2008 | Jambor et al. |
| 7,366,571 B2 | 4/2008 | Armstrong |
| 7,367,340 B2 | 5/2008 | Nelson |
| 7,367,937 B2 | 5/2008 | Jambor |
| 7,374,565 B2 | 5/2008 | Hassler, Jr. |
| 7,390,294 B2 | 6/2008 | Hassler |
| 7,396,353 B2 | 7/2008 | Lorenzen |
| 7,416,528 B2 | 8/2008 | Crawford et al. |
| 7,481,763 B2 | 1/2009 | Hassler |
| 7,500,944 B2 | 3/2009 | Byrum |
| 7,530,943 B2 | 5/2009 | Lechner |
| 7,594,885 B2 | 9/2009 | Byrum |
| 7,599,743 B2 | 10/2009 | Hassler |
| 7,599,744 B2 | 10/2009 | Giordano |
| 7,601,162 B2 | 10/2009 | Hassler, Jr. et al. |
| 7,615,001 B2 | 11/2009 | Jambor |
| 7,618,365 B2 | 11/2009 | Jambor |
| 7,658,196 B2 | 2/2010 | Ferreri |
| 7,699,770 B2 | 4/2010 | Hassler |
| 7,727,141 B2 | 6/2010 | Hassler, Jr. et al. |
| 7,758,493 B2 | 7/2010 | Gingras |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,794,386 B2 | 9/2010 | Brooks |
| 7,811,298 B2 | 10/2010 | Birk |
| 7,844,342 B2 | 11/2010 | Dlugos et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0139208 A1 | 10/2002 | Yatskov |
| 2002/0193679 A1 | 12/2002 | Malave et al. |
| 2002/0198548 A1 | 12/2002 | Robert |
| 2003/0019498 A1 | 1/2003 | Forsell |
| 2003/0045775 A1 | 3/2003 | Forsell |
| 2003/0055311 A1 | 3/2003 | Neukermans et al. |
| 2003/0066536 A1 | 4/2003 | Forsell |
| 2003/0073880 A1 | 4/2003 | Polsky et al. |
| 2003/0158569 A1 | 8/2003 | Wazne |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0059393 A1 | 3/2004 | Policker et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |

(56) References Cited

U.S. PATENT DOCUMENTS

| | | |
|---|---|---|
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum |
| 2004/0267291 A1 | 12/2004 | Byrum et al. |
| 2004/0267292 A1 | 12/2004 | Byrum |
| 2004/0267293 A1 | 12/2004 | Byrum et al. |
| 2004/0267377 A1 | 12/2004 | Egle |
| 2005/0002984 A1 | 1/2005 | Byrum |
| 2005/0038484 A1 | 2/2005 | Knudson et al. |
| 2005/0055039 A1 | 3/2005 | Burnett et al. |
| 2005/0070934 A1 | 3/2005 | Tanaka et al. |
| 2005/0070937 A1 | 3/2005 | Jambor |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0143765 A1 | 6/2005 | Bachmann et al. |
| 2005/0143766 A1 | 6/2005 | Bachmann et al. |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0216042 A1 | 9/2005 | Gertner |
| 2005/0228415 A1 | 10/2005 | Gertner |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1* | 11/2005 | Coe ........................ 600/31 |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler et al. |
| 2005/0267533 A1 | 12/2005 | Gertner |
| 2005/0277899 A1 | 12/2005 | Conlon et al. |
| 2005/0283041 A1 | 12/2005 | Egle |
| 2005/0288739 A1 | 12/2005 | Hassler |
| 2005/0288740 A1 | 12/2005 | Hassler |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0161186 A1 | 7/2006 | Hassler, Jr. et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler |
| 2006/0189888 A1 | 8/2006 | Hassler |
| 2006/0189889 A1 | 8/2006 | Gertner |
| 2006/0195139 A1 | 8/2006 | Gertner |
| 2006/0197412 A1 | 9/2006 | Rasmussen |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0212053 A1 | 9/2006 | Gertner |
| 2006/0235448 A1 | 10/2006 | Roslin et al. |
| 2006/0247722 A1 | 11/2006 | Maschino et al. |
| 2006/0247724 A1 | 11/2006 | Gerber et al. |
| 2006/0252982 A1 | 11/2006 | Hassler, Jr. et al. |
| 2006/0264699 A1 | 11/2006 | Gertner |
| 2006/0276812 A1 | 12/2006 | Hill et al. |
| 2007/0015954 A1 | 1/2007 | Dlugos |
| 2007/0015955 A1 | 1/2007 | Tsonton |
| 2007/0016262 A1 | 1/2007 | Gross et al. |
| 2007/0027356 A1 | 2/2007 | Ortiz |
| 2007/0078476 A1 | 4/2007 | Hull et al. |
| 2007/0125826 A1 | 6/2007 | Shelton |
| 2007/0156013 A1* | 7/2007 | Birk ........................ 600/37 |
| 2007/0167672 A1 | 7/2007 | Dlugos et al. |
| 2007/0185462 A1 | 8/2007 | Byrum |
| 2007/0218083 A1 | 9/2007 | Brooks |
| 2007/0232848 A1 | 10/2007 | Forsell |
| 2007/0235083 A1 | 10/2007 | Dlugos |
| 2007/0250085 A1 | 10/2007 | Bachmann et al. |
| 2007/0250086 A1 | 10/2007 | Wiley |
| 2007/0255336 A1 | 11/2007 | Herbert et al. |
| 2007/0265598 A1 | 11/2007 | Karasik |
| 2007/0265645 A1 | 11/2007 | Birk et al. |
| 2008/0009680 A1 | 1/2008 | Hassler |
| 2008/0015406 A1 | 1/2008 | Dlugos |
| 2008/0027469 A1 | 1/2008 | Bachmann |
| 2008/0097496 A1 | 4/2008 | Chang et al. |
| 2008/0108862 A1 | 5/2008 | Jordan et al. |
| 2008/0166028 A1 | 7/2008 | Turek et al. |
| 2008/0221598 A1 | 9/2008 | Dlugos |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0157106 A1 | 6/2009 | Marcotte |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe |
| 2009/0171379 A1 | 7/2009 | Coe et al. |
| 2009/0192404 A1 | 7/2009 | Ortiz |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz |
| 2009/0204132 A1 | 8/2009 | Ortiz |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1* | 8/2009 | Coe et al. ........................ 606/157 |
| 2009/0222031 A1 | 9/2009 | Axelsson |
| 2009/0222065 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2009/0312785 A1 | 12/2009 | Stone et al. |
| 2010/0010291 A1 | 1/2010 | Birk |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0152532 A1 | 6/2010 | Marcotte |
| 2010/0185049 A1 | 7/2010 | Birk et al. |
| 2010/0191271 A1 | 7/2010 | Lau et al. |
| 2010/0228080 A1 | 9/2010 | Tavori et al. |
| 2010/0249803 A1 | 9/2010 | Griffiths |
| 2010/0280310 A1 | 11/2010 | Raven |
| 2010/0305397 A1 | 12/2010 | Birk et al. |
| 2010/0324358 A1 | 12/2010 | Birk et al. |
| 2010/0324359 A1 | 12/2010 | Birk |

FOREIGN PATENT DOCUMENTS

| | | |
|---|---|---|
| DE | 4225524 | 2/1994 |
| DE | 10020688 | 12/2000 |
| EP | 0119596 | 9/1984 |
| EP | 0230747 | 8/1987 |
| EP | 0611561 | 8/1994 |

(56) References Cited

FOREIGN PATENT DOCUMENTS

| | | |
|---|---|---|
| EP | 0695558 | 2/1996 |
| EP | 0867808 | 11/1998 |
| EP | 1072282 | 1/2001 |
| EP | 1396242 | 3/2004 |
| EP | 1396243 | 3/2004 |
| EP | 1491167 | 12/2004 |
| EP | 1547549 | 6/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 2074970 | 7/2009 |
| EP | 2074971 | 7/2009 |
| EP | 2087862 | 8/2009 |
| EP | 2095796 | 9/2009 |
| EP | 2095798 | 9/2009 |
| FR | 2797181 | 2/2001 |
| FR | 2823663 | 10/2002 |
| FR | 2855744 | 12/2004 |
| FR | 2921822 | 4/2009 |
| JP | 2005-334658 | 12/2005 |
| WO | WO 89/11701 | 11/1989 |
| WO | WO 00/09047 | 2/2000 |
| WO | WO 00/09048 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 01/70131 | 9/2001 |
| WO | WO 02/26317 | 4/2002 |
| WO | WO 02/053093 | 7/2002 |
| WO | WO 02/065948 | 8/2002 |
| WO | WO 03/077191 | 9/2003 |
| WO | WO 03/105732 | 12/2003 |
| WO | WO 2004/014245 | 2/2004 |
| WO | WO 2004/019671 | 3/2004 |
| WO | WO 2005/007232 | 1/2005 |
| WO | WO 2005/009305 | 2/2005 |
| WO | WO 2005/087147 | 9/2005 |
| WO | WO 2005/094447 | 10/2005 |
| WO | WO 2006/083885 | 8/2006 |
| WO | WO 2006/108203 | 10/2006 |
| WO | WO 2008/109300 | 9/2008 |
| WO | WO 2009/132127 | 10/2009 |

OTHER PUBLICATIONS

Corno et al.; "FloWatchTM in clipped and inclipped position," Interact Cardio Vase Thorac Surg 2002; 1:46-49.

BioEnterics Lap-Band Adjustable Gastric Banding System, Inamed Health, pub. Aug. 28, 2003 pp. 1-115.

Iverson et al.; "Recent Advances in Microscale Pumping Technologies: A Review and Evaluation"; Microfluid Nanofluid; vol. 5; pp. 145-174; Feb. 19, 2008.

\* cited by examiner

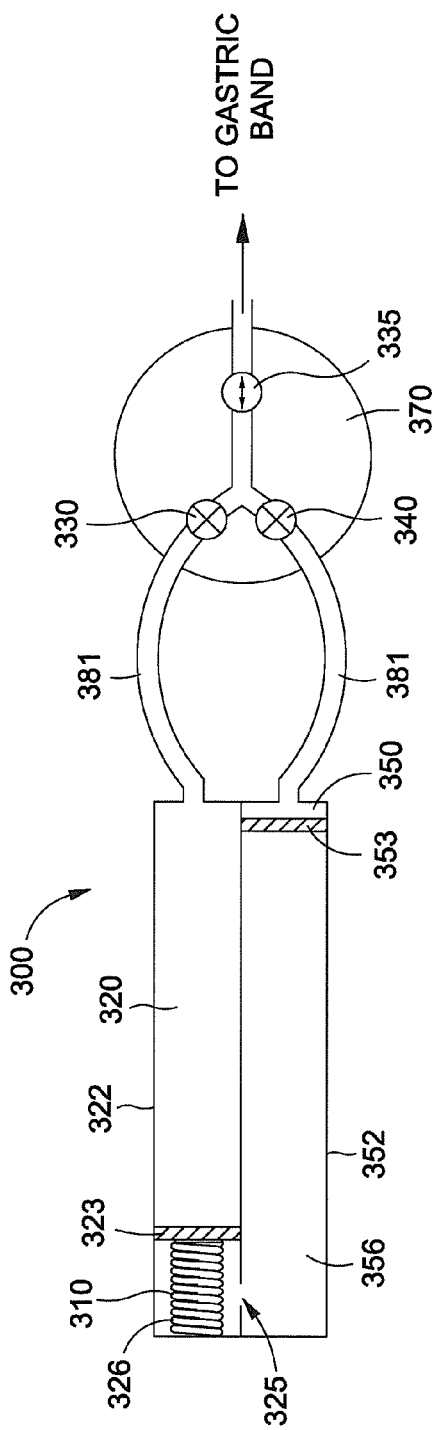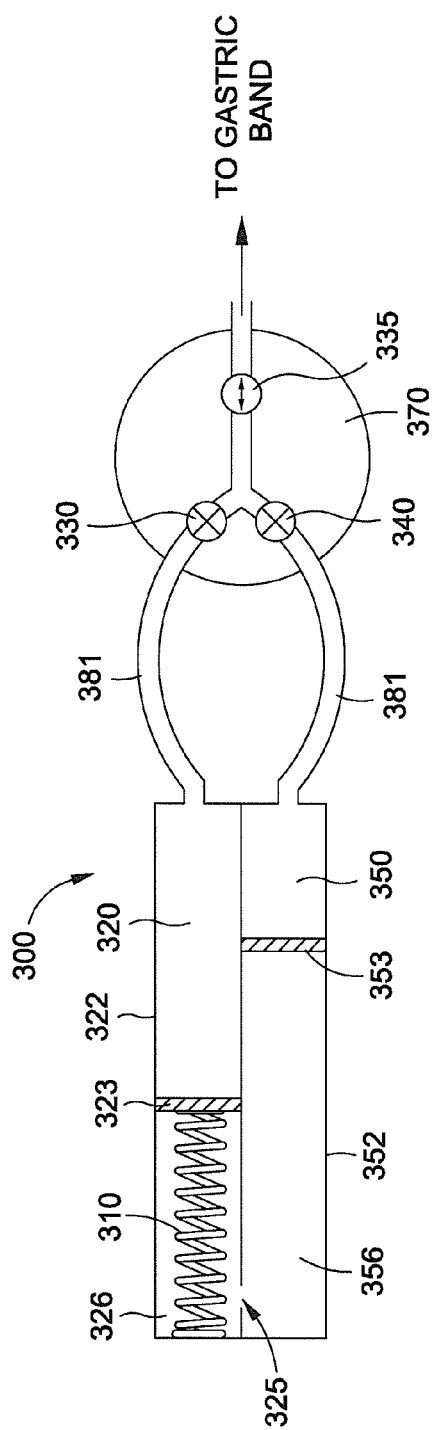
FIG. 3A
FIG. 3B

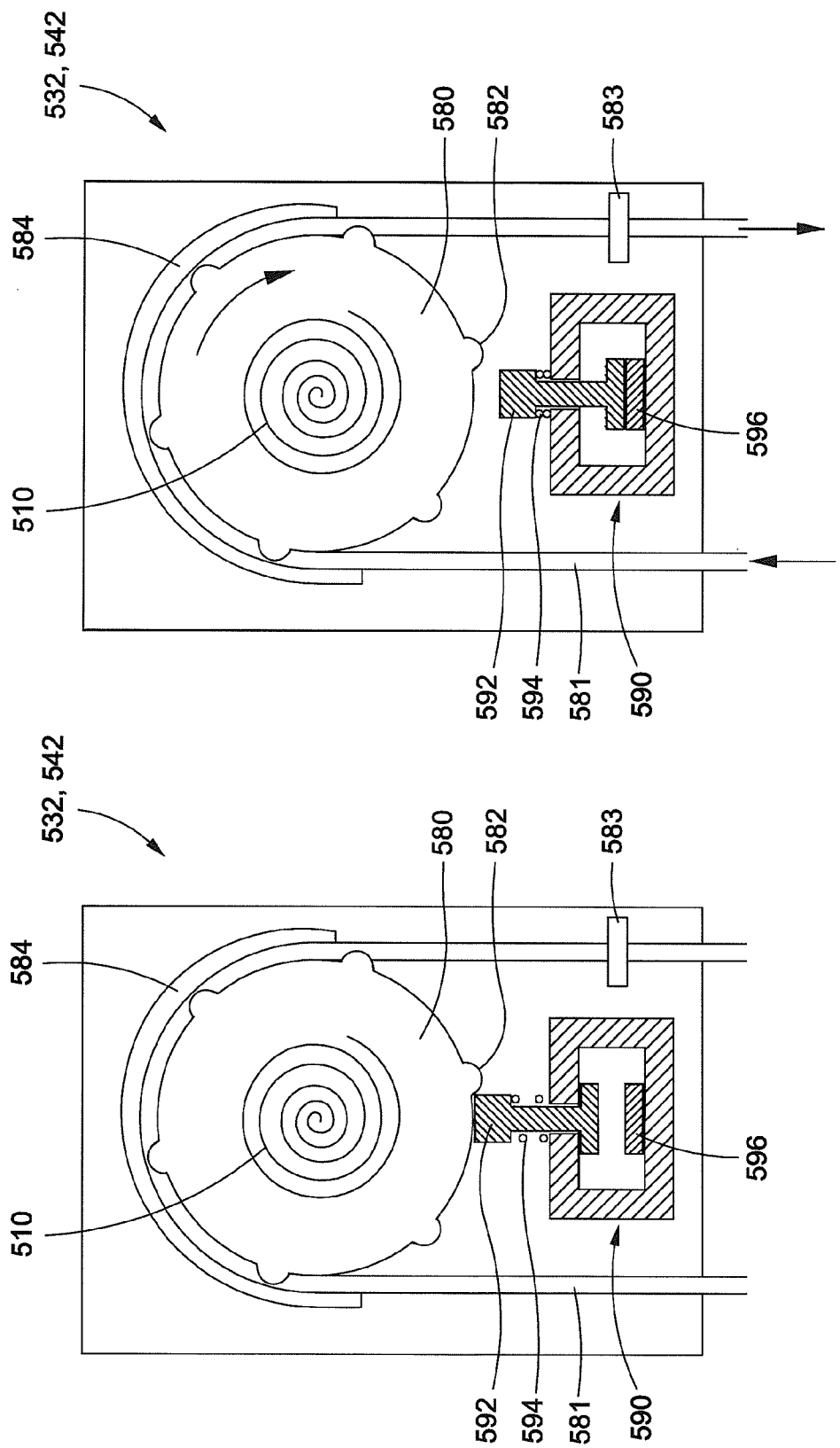

REMOTELY ADJUSTABLE GASTRIC BANDING SYSTEM

FIELD

The present invention generally relates to medical systems and apparatus and uses thereof for treating obesity and/or obesity-related diseases, and more specifically, relates to gastric banding systems that are remotely adjustable using stored potential energy.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the passage of food into a lower portion of the stomach. When the stoma is of an appropriate size that is restricted by a gastric band, food held in the upper portion of the stomach provides a feeling of satiety or fullness that discourages overeating. Unlike gastric bypass procedures, the gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Naturally, it would be desirable to allow for non-invasive adjustment of gastric band constriction, for example, without the use of a hypodermic needle. Thus, remotely adjustable gastric banding systems have been proposed and are described herein.

Furthermore, some remotely adjustable gastric banding systems have been proposed, but these remote systems generally utilize significant external power in order to power pumps associated with the remotely adjustable systems. Thus, remotely adjustable gastric banding systems that utilize reduced power from an external transmitter are disclosed herein.

SUMMARY

Generally described herein are remotely adjustable and powered gastric band systems, and methods of use thereof. The apparatus, systems and methods described herein aid in facilitating obesity control and/or treating obesity-related diseases while being non-invasive once implanted.

In an embodiment, an implantable device uses potential energy to facilitate the movement of fluid to an inflatable portion of a gastric band, and the implantable device comprises a filling reservoir for holding the fluid. The implantable device further comprises a first device operatively coupled to the filling reservoir, and the first device comprises stored potential energy that facilitates moving an amount of the fluid to the inflatable portion of the gastric band.

Additionally, the implantable device comprises a filling valve coupled between the filling reservoir and the gastric band, and the filling valve may be open or closed based on a first telemetric signal received from a remote transmitter. When the filling valve is open, a portion of the stored potential energy is released causing the amount of the fluid to move from the filling reservoir into the inflatable portion of the gastric band. When the filling valve is closed, a remaining amount of the stored potential energy remains stored in the first device.

The implantable device further comprises a draining reservoir and a draining valve coupled between the draining reservoir and the gastric band. The draining valve may be opened or closed based on a second telemetric signal received from the remote transmitter. A portion of the fluid in the inflatable portion of the gastric band moves into the draining reservoir when the draining valve is open. A flow meter is coupled to the filling valve and/or the draining valve to determine an amount of the fluid moving into or out of the inflatable portion of the gastric band. The filling valve and the draining valve are powered by inductive powering signals received from the remote transmitter.

In various embodiments, the implantable device further comprises a filling chamber that includes the filling reservoir and a filling pressure section. A filling piston separates the filling reservoir and the filling pressure section. The implantable device also comprises a draining chamber that includes the draining reservoir and a draining pressure section. A draining piston separates the draining reservoir and the draining pressure section. A pressure port connects the filling chamber and the draining chamber and facilitates equalizing a pressure in the filling pressure section and the draining pressure section. The draining chamber is sealed such that the draining piston cannot move unless the draining valve is open.

The first device is operatively coupled to the filling piston, and the filling chamber is sealed such that the filling piston cannot move unless the filling valve is open. When the filling valve is open, the filling piston moves from a first position to a second position in response to the portion of the stored potential energy being released. A volume of fluid in the filling reservoir is displaced when the filling piston moves from the first position to the second position.

Further, a vacuum pressure is generated in the filling pressure section and in the draining pressure section when the filling piston moves from the first position to the second position, and this vacuum pressure exerts a draining force on the draining piston. The vacuum pressure causes the draining piston to move from a third position to a fourth position when the draining valve is open, and a draining amount of the fluid is removed from the gastric band when the draining piston moves from the third position to the fourth position.

Additionally, in various embodiments, the implantable device comprises a sealed chamber that includes the filling reservoir and the draining reservoir. A piston is disposed between the filling reservoir and the draining reservoir and between a filling end of the sealed chamber and a draining end of the sealed chamber. The filling valve is coupled to the filling end and the draining valve is coupled to the draining end, and the piston moves toward the filling end of the sealed chamber when the portion of the stored potential energy is released. The volume of the filling reservoir and the volume of the draining reservoir change as the piston moves in the sealed chamber.

A vacuum pressure is generated in the draining reservoir when the piston moves toward the filling end of the sealed chamber. The vacuum pressure causes a draining amount of the fluid to be removed from the gastric band when the draining valve is open, and the draining amount of the fluid moves into the draining reservoir from the gastric band.

In accordance with an embodiment, the implantable device comprises a filling peristaltic pump operatively coupled to the filling reservoir and the gastric band. Also, the implantable device comprises a draining peristaltic pump operatively coupled to the gastric band and the draining reservoir. The first device is disposed within the filling peristaltic pump, and the filling peristaltic pump comprises an arresting mechanism. Further, the first device releases the portion of the stored potential energy when the arresting mechanism in the pump is deactivated.

Moreover, according to an embodiment, an implantable device comprises a reservoir that contains a fluid for filling an inflatable portion of a gastric band. A device is coupled to the reservoir and includes stored potential energy having a first state and a second state. The first state represents a higher level of potential energy and the second state represents a lower level of potential energy. The implantable device further comprises a filling valve coupled between the reservoir and the gastric band, and the filling valve is configured to be opened in response to a first telemetric signal. The stored potential energy decreases from the first state to the second state when the filling valve is open, and a filling amount of the fluid moves from the reservoir to the gastric band when the stored potential energy decreases from the first state to the second state.

A method for adjusting an inflatable gastric band of a gastric banding system according to various embodiments comprises opening a filling valve of the gastric banding system using a first telemetric signal, and releasing an amount of stored potential energy in a device coupled to a filling reservoir of the gastric banding system. The method further comprises moving a filling amount of fluid from the filling reservoir to the inflatable gastric band when the amount of the stored potential energy is released, and reading a flow meter using a second telemetric signal to determine that the filling amount has been moved into the inflatable gastric band. The filling valve is then closed using a third telemetric signal.

To remove fluid from the gastric band, a draining valve of the gastric banding system is opened with a fourth telemetric signal. An amount of stored energy is then utilized to move a draining amount of fluid from the inflatable gastric band to the draining reservoir. The flow meter may be read using a fifth telemetric signal to determine that the draining amount has been moved out of the inflatable gastric band. The draining valve may be closed using a sixth telemetric signal.

BRIEF DESCRIPTION OF THE DRAWINGS

FIGS. 3A and 3B illustrate a reservoir and valve configuration of a gastric banding system according to an embodiment of the present invention.

FIGS. 5C-5D illustrate sectional views of peristaltic pumps as represented in FIG. 5A according to an embodiment of the present invention.

DETAILED DESCRIPTION

The present invention generally provides remotely adjustable gastric banding systems, for example, for treatment of obesity and obesity related conditions, as well as systems for controlling inflation of gastric banding systems.

Figure 1:
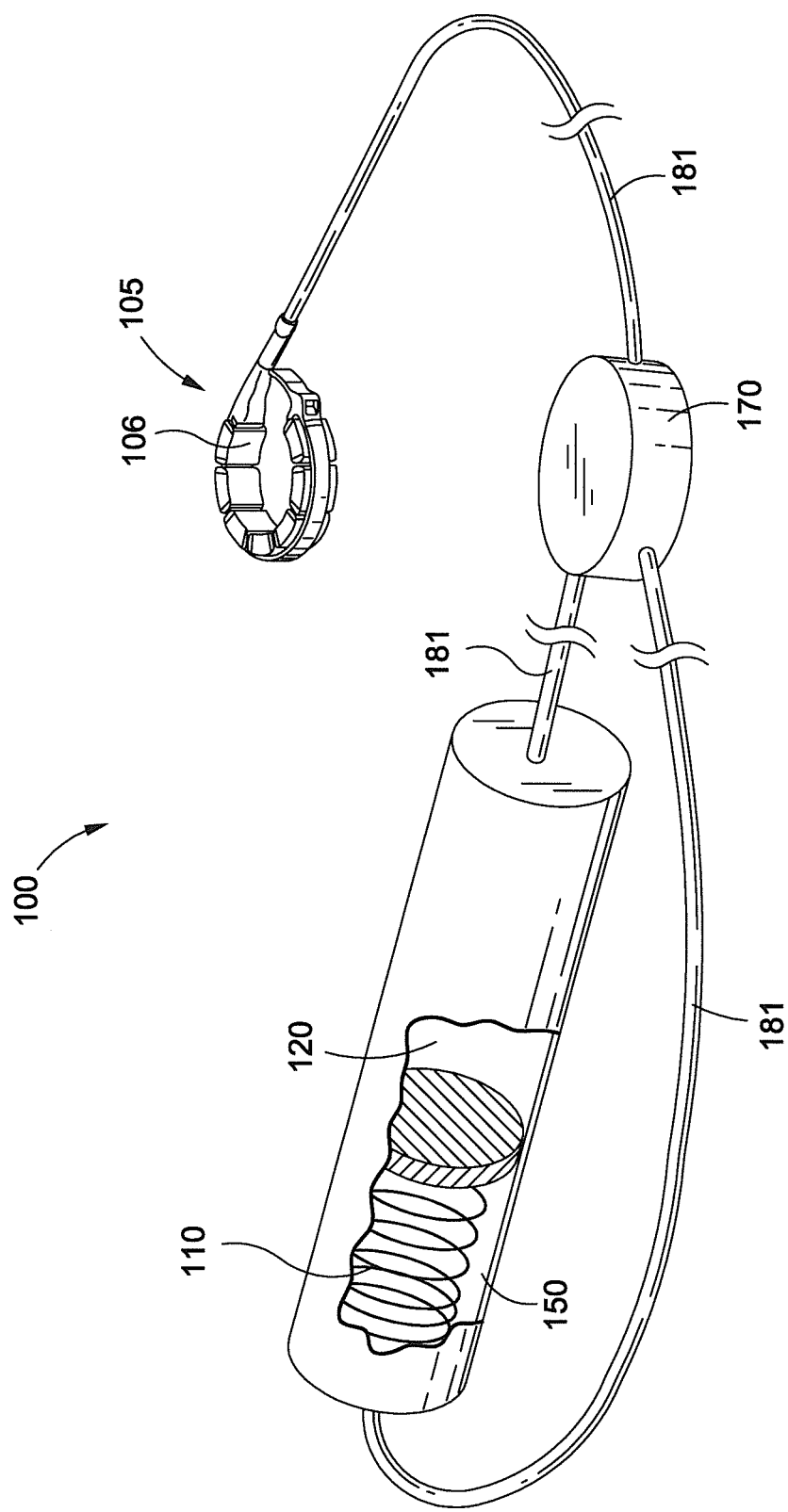
FIG. 1 illustrates a perspective view of a gastric banding system according to an embodiment of the present invention.

Turning now to FIG. 1, a gastric banding system 100 in accordance with one embodiment of the present invention generally includes a gastric band 105, a filling reservoir 120, a draining reservoir 150, an energy storage device 110, and a junction box 170. Each of the components of system 100 is implantable in a patient using conventional surgical techniques. The filling reservoir 120, the draining reservoir 150, and the energy storage device 110 may be used to replace or complement a conventional access port for adjusting inflation of the gastric band 105. In some embodiments, the system includes a conventional access port which can be used, for example, with a hypodermic needle, to fill and drain the gastric band 105.

The filling reservoir 120 and the energy storage device 110 may move precisely metered volumes of a fluid (e.g., saline) through the junction box 170 into the gastric band 105. Moving the fluid into the gastric band 105 causes inflation of at least one bladder, or an inflatable member 106 and constricts around the cardia, or upper portion of the stomach, forming a stoma that restricts the passage of food into a lower portion of the stomach. This stoma can provide a patient with a sensation of satiety or fullness that discourages overeating.

In contrast, moving the fluid out of at least one inflatable member 106 of the gastric band 105 contracts the pressure around the cardia and allows a stoma to be at least partially released and regains the patient's hunger sensation. The draining reservoir 150 and the junction box 170 facilitate moving the fluid out of the gastric band 105. Although the draining reservoir 150 may be described herein as a compartment that receives fluid from the gastric band 105, it should be understood that the draining reservoir 150 in various embodiments may be the peritoneal cavity of a patient's body.

The energy storage device 110 may comprise a balloon, a peristaltic pump, a piston, a plunger, a compression spring, an extension spring, and combinations thereof. Furthermore, the energy storage device 110 may comprise any device that stores potential energy which may be released in response to a telemetric signal from a transmitter external to a patient's body.

The fluids used within the systems of the present description include any fluid that is biocompatible and incompressible. The fluid has no adverse effect on the patient in the unlikely event that a leak emanates from the system. The fluid can simply be water or any biocompatible polymer oil such as castor oil. In an example embodiment, the fluid is saline.

Tubing 181 connects the various components of the system 100 and comprises any biocompatible flexible tubing that does not degrade in vivo. The tubing 181 is configured to withstand hydraulic forces up to about 30 psi (about 206 kPa) without leakage. This hydraulic pressure tolerance is true of the entire fluid path of the systems described herein. Although the systems described herein do not generally leak, if they do, fluid is not lost at a rate greater than about 0.2 cc/yr, or about 0.1 cc/yr.

According to various embodiments, components of the gastric banding system 100 may be placed in their respective positions within a patient using common surgical techniques. The surgical techniques may be similar to those used in the placement of conventional gastric banding systems. For example, the gastric band 105 may be placed around the stomach using laparoscopic techniques, as known to those of skill in the art. Like a conventional access port, various components of the gastric banding system 100 may be sutured onto the rectus muscle sheath or any other conveniently accessible muscle. In order to achieve a secure attachment of the components, the components may be sutured to the rectus muscle and remain securely attached for forces below about 6 lbf, preferably below about 3 lbf (13.3 N). The tubing 181 to the gastric band 105 passes through the rectus muscle into the peritoneal cavity in the same or similar manner as the tubing of a conventional access port.

Figure 2:
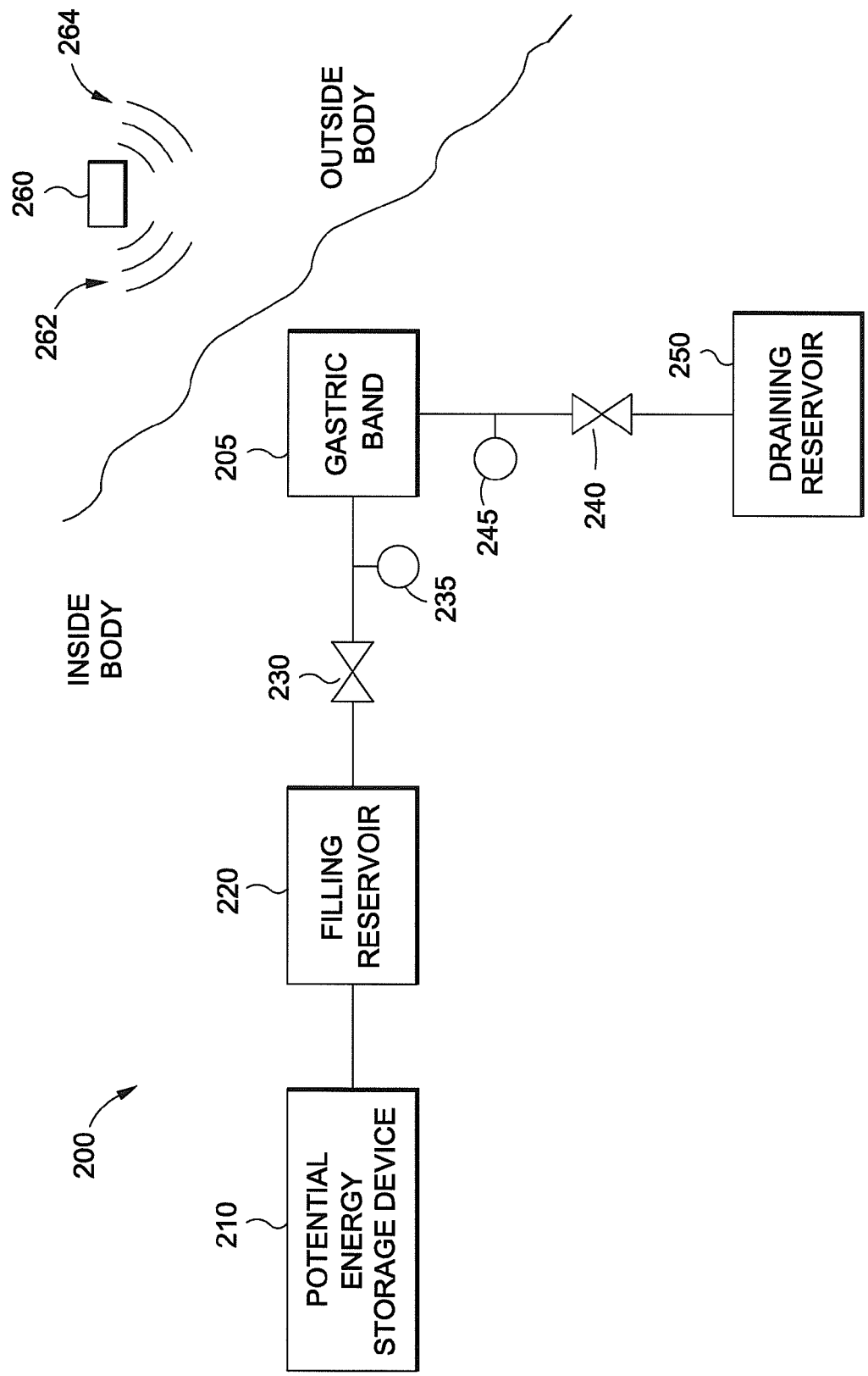
FIG. 2 illustrates an example configuration of a gastric banding system according to an embodiment of the present invention.

FIG. 2 illustrates a schematic of a gastric banding system 200, which comprises a filling valve 230 and a filling flow meter 235 coupled between the filling reservoir 220 and the gastric band 205. The system 200 further comprises a draining valve 240 and a draining flow meter 245 coupled between the gastric band 205 and the draining reservoir 250. One flow meter may be used instead of separate filling flow meter 235 and draining flow meter 245, but two flow meters are illustrated here for purposes of describing the functionality of the gastric banding system 200.

The filling flow meter 235 and the filling valve 230 are interoperable to control an amount of fluid that enters the gastric band 205. When additional fluid is desired in the gastric band 205, the potential energy storage device 210 exerts a force on the fluid in the filling reservoir 220 such that when the filling valve 230 is opened, fluid is moved from the filling reservoir 220 to the gastric band 205. When the filling valve 230 remains closed, potential energy from the storage device 210 is not released, and the fluid does not flow from the filling reservoir 220 to the gastric band 205. The filling flow meter 235 is utilized to determine that an appropriate amount of the fluid has entered the gastric band 205.

Similarly, the draining valve 240 and the draining flow meter 245 are interoperable to reduce an amount of fluid in the gastric band 205 to a desired level. For example, when the valve 240 is opened, the fluid may flow from the gastric band 205 to the draining reservoir 250. The draining flow meter 240 may measure the amount of fluid exiting the gastric band 205 to facilitate obtaining an appropriate inflation of the gastric band 205.

The valves 230 and 240 can be any valve known in the art to allow precise delivery of the fluid and precise flow rates through the valves in response to the inductive powering signals received from a remote transmitter. For example, piezoelectric valves, solenoid valves, and combinations thereof may be utilized. Further, the valves 230 and 240 may have a precision orifice that restricts the flow rate to a well-characterized, precise amount.

The filling valve 230 and the draining valve 240 are controlled telemetrically by a device, such as a remote transmitter 260, that is external to a patient's body. The remote transmitter 260 controls the valves 230 and 240 via the wireless signals 262 and 264 (e.g., radio frequency signals). These wireless signals 262 and 264 provide inductive power to the valves 230 and 240 to facilitate opening and closing of the valves 230 and 240. In various embodiments, the wireless signal 262 powers the filling valve 230 and the wireless signal 264 powers the draining valve 240. However, it should be understood that the transmitter 260 may be configured to utilize any number of signals and frequencies to communicate with components of the system 200.

Although "transmitter" may be used herein, in should be understood that the remote transmitter 260 may also be a wireless receiver and/or transceiver operable to take readings from the flow meters 235 and 245 to determine the amount of the fluid entering and/or exiting the gastric band 205, and/or to send or receive other types of information associated with the gastric banding system 200.

In various embodiments, the remote transmitter 260 provides access to system data and functions and is an external, handheld, reusable battery-powered device. The remote transmitter 260 can be made of any rugged plastic material including, polypropylene, cyclicolefin co-polymer, nylon, and other compatible polymers and the like. Further, the remote transmitter 260 has a user interface including at least one display and at least one user input. The remote transmitter 260 permits a clinician or a patient to navigate through menu driven screens used for data entry, data collection, and control of the gastric banding system 200.

The remote transmitter 260 is capable of communicating with the gastric banding system 200. "Capable of communicating" as used herein refers to the remote transmitter's ability to establish communications with the gastric banding system 200, yet still have the ability to break communication and the systems described herein still function. To establish communication, in one example embodiment, once the remote transmitter 260 is initialized, a display shows a searching query for a nearby gastric banding system 200. As the remote transmitter 260 is brought within a range of the gastric banding system 200, the display shows the strength of the communication link. Once stable communications have been acquired, the display shows the serial number of the system so a clinician can verify they have the appropriate patient records in hand. If the patient requires a tightening of the gastric band 205, the clinician can enter the amount of the desired volume increase. The remote transmitter 260 can also display the current volume within the gastric band 205 and indicate the new volume as the gastric band 205 fills. The remote transmitter 260 can also indicate desired and actual volumes during the gastric band 205 draining.

In accordance with various embodiments, the gastric banding system 200 allows for a remotely controlled adjustment without needles, non-invasively, by using the remote transmitter 260. When compared to conventional gastric banding systems having standard access ports which exclusively require syringe access, the presently described systems and apparatus offer several benefits. First, for conventional access ports located under a thick layer of fatty tissue, which is generally the case as the devices are generally used to treat obesity, the access port can be difficult to locate. The present systems reduce or eliminate the need for port location as the use of the remote transmitter 260 removes the necessity of adjustment using a syringe.

Second, accessing the access port in conventional systems, when there is ambiguity on its location, can cause damage by accidentally puncturing the tubing which connects the access port to the gastric band. This damage can require a revision surgery in order to repair the punctured tubing. Further, when a conventional access port cannot be located by palpation, x-ray imaging may be required to guide a needle into the access port. Such imaging practices put a patient at risk for x-ray radiation exposure. The present systems and apparatus remove the need for these unnecessary procedures and save the patient from x-ray radiation exposure. As described herein, the present systems and apparatus are compatible with magnetic resonance imaging (MRI), which is much safer for a patient.

However, should the remote transmitter 260 be unavailable, damaged, out of power, or in the event of an emergency, an adjustment of the gastric band 205 may be performed invasively using a needle. For example, an access port (commonly used in other gastric banding systems) may be included in the gastric banding system 205, in addition to the other components illustrated in FIG. 2. The access port may be located between the valves 230 and 240 and the gastric band 205 (for example, in a junction box 370 between the valves 330 and 340 and the flow meter 335 as illustrated in FIG. 3A).

Thus, a clinician may choose to use a standard needle for adjustments, for example, if any of the electronics associated with the gastric banding system 200 become inoperable. Even if the electronics are unavailable, the access port would be available to adjust the gastric band 205. In the unlikely event that the access port is used, it may be located away from the tubing connection to the gastric band 205 to reduce the potential for tubing needle sticks. Information regarding hydraulically adjustable gastric banding systems including subcutaneous fluid access ports/injection ports may be found in Vincent, U.S. Pat. No. 5,601,604; Kusmack, U.S. Pat. No. 5,226,429; Birk, U.S. Patent Application Publication No. 2005/0192531, the disclosure of each of these patents and publications is being incorporated herein in its entirety by this specific reference.

In accordance with various embodiments, the gastric banding system 200 provides advantages over other existing gastric banding systems that utilize inductive powering to drive pumps to fill and drain a gastric band. Such existing systems require substantial power to drive these internal pumps (e.g., piezoelectric pumps), and these pumps may be subject to low flow rates. With greater power, the pumps may heat up more and dissipate more heat within the patient. Less power is utilized in the gastric banding system 200, because the valves 230 and 240 need only to be opened or closed using the remote transmitter 260. Power to drive the fluid flow is provided by the stored potential energy, and this fluid flow may be carried out at a higher rate than in existing systems. Thus, the gastric banding system 200 is more efficient than existing gastric banding systems that use non-invasive adjustment methods.

Turning now to FIGS. 3A-3B, an embodiment of the gastric banding system 300 comprises a filling chamber 322 that includes the filling reservoir 320 and a filling piston 323. The filling reservoir 320 contains a fluid, such as saline, that is utilized to fill a gastric band. In various embodiments, approximately 10 mL of the fluid may be contained in the filling reservoir 320. The filling piston 323 is driven by a compression spring 310 to pump the fluid from the filling reservoir 320 to the gastric band.

The system 300 further comprises a draining chamber 352 that includes a draining reservoir 350 and a draining piston 353 to facilitate pumping the fluid from the gastric band into the draining reservoir 350. The draining chamber 352 is connected to the filling chamber 322 by a pressure port 325 that facilitates equalizing an air pressure between a filling pressure section 326 of the filling chamber 322 and a draining pressure section 356 of the draining chamber 352.

The chambers 322 and 352 are connected to a gastric band using the flexible tubing 381 and the junction box 370. The junction box 370 comprises the filling valve 330, the draining valve 340, and the flow meter 335. The filling valve 330 connects the filling reservoir 320 to the flow meter 335, and the draining valve 370 connects the draining reservoir 350 to the flow meter 335. Such a configuration allows the flow meter 335 to monitor all the fluid flowing into and out of the gastric band.

The filling chamber 322 and the draining chamber 352 are hermetically sealed with respect to the patient's body. As mentioned above, in an embodiment, the filling chamber 322 and draining chamber 352 are not sealed from each other, but are connected via the pressure port 325.

The spring 310 is designed to have sufficient potential energy to enable the piston 323 to move a desired amount of the fluid from the filling reservoir 320 into the gastric band. For example, the inflatable portion of the gastric band has a certain amount of resistance, and the spring 310 is configured to contain sufficient potential energy to overcome this resistance. Thus, when the valve 330 is opened, some potential energy is released from the spring 310, causing the piston 323 to move within the filling chamber 322 to expel some fluid from the filling reservoir 320 into the gastric band.

Because the chamber 322 is sealed, when the filling valve 330 opens and the spring 310 drives the piston 323 to move the fluid out of the filling reservoir 320 into the gastric band, a vacuum pressure is developed in the pressure portion 326 of the filling chamber 322. The generated vacuum pressure is not sufficient to prevent the piston 323 from moving within the chamber 322 when the filling valve 330 is opened. As noted, the pressure port 325 facilitates equalizing the pressure between the pressure portion 326 of the filling chamber 322 and the pressure portion 356 of the draining chamber 352, causing this vacuum pressure to also exist in the draining pressure section 356.

This vacuum pressure exerts a force on the draining piston 353 that is sufficient to cause the draining piston 353 to move within the chamber 352 when the draining valve 340 is opened. It should be noted that the vacuum pressure exerts an equal force on the filling piston 323. However, the filling valve 330 remains closed when the draining valve 340 is opened, preventing the filling piston 323 from moving in response to the vacuum pressure. The system 300 is designed such that the vacuum pressure generated in the pressure portions 326 and 356 provides a force on the draining piston 353 sufficient to allow the gastric band to reach a predetermined state after draining of the fluid. For example, the draining reservoir 350 may be configured to receive a portion of and/or all the fluid inserted into the gastric band from the filling reservoir 320.

The valves 330 and 340 may be alternately opened and closed until all and/or substantially all the fluid from the filling reservoir 320 has been depleted and moved into the draining reservoir 350. In an embodiment, this condition represents an end-of-life of the gastric banding system 300. Sufficient fluid may be contained within the filling reservoir 320 to provide a life cycle for the gastric banding system 300 of up to ten or more years, depending on the frequency of gastric band adjustments.

In an embodiment, the gastric banding system 300 may incorporate a fluid port configured to refill the filling reservoir 320 and/or to drain the draining reservoir 350. This fluid port may be configured to provide sufficient pressure to compress the spring 310 and restore the potential energy to the system 300 in order to lengthen the life cycle of the system 300. In various embodiments, a fluid port may be coupled directly to the gastric band and/or to some other portion of the system 300 (e.g., in the junction box 370, between the valves 330 and 340 and the flow meter 335) to facilitate inflating and/or deflating the gastric band independently of the reservoirs 320 and 350.

Figure 4A:
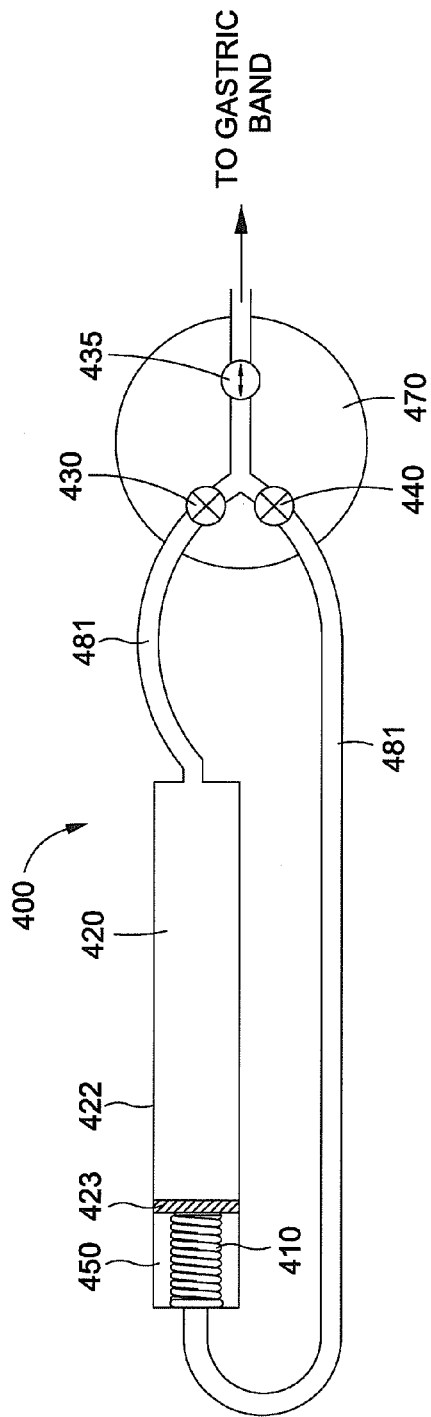
FIGS. 4A and 4B illustrate a single chamber injection-type device and valve configuration according to an embodiment of the present invention.
Figure 4B:
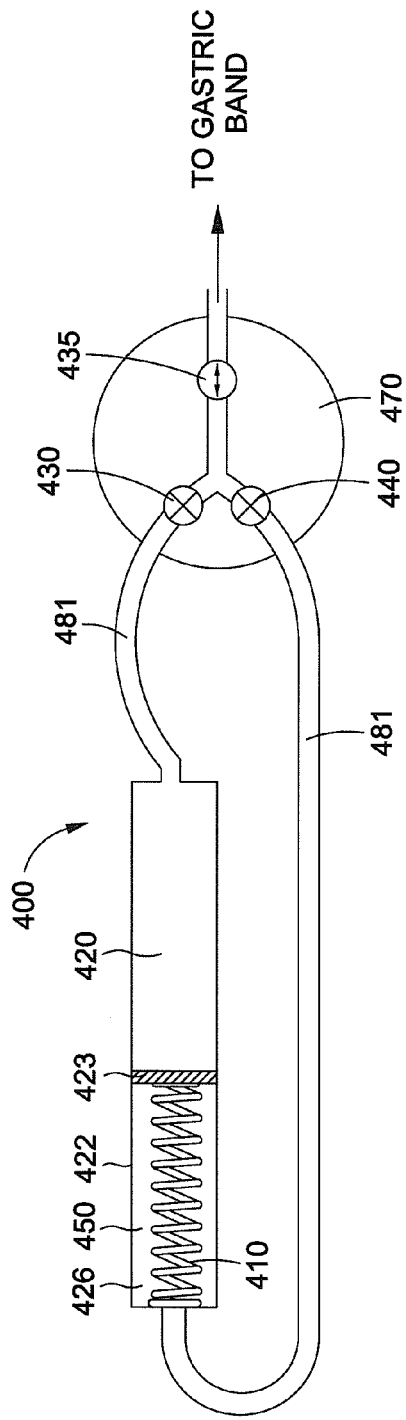
Figure 5A:
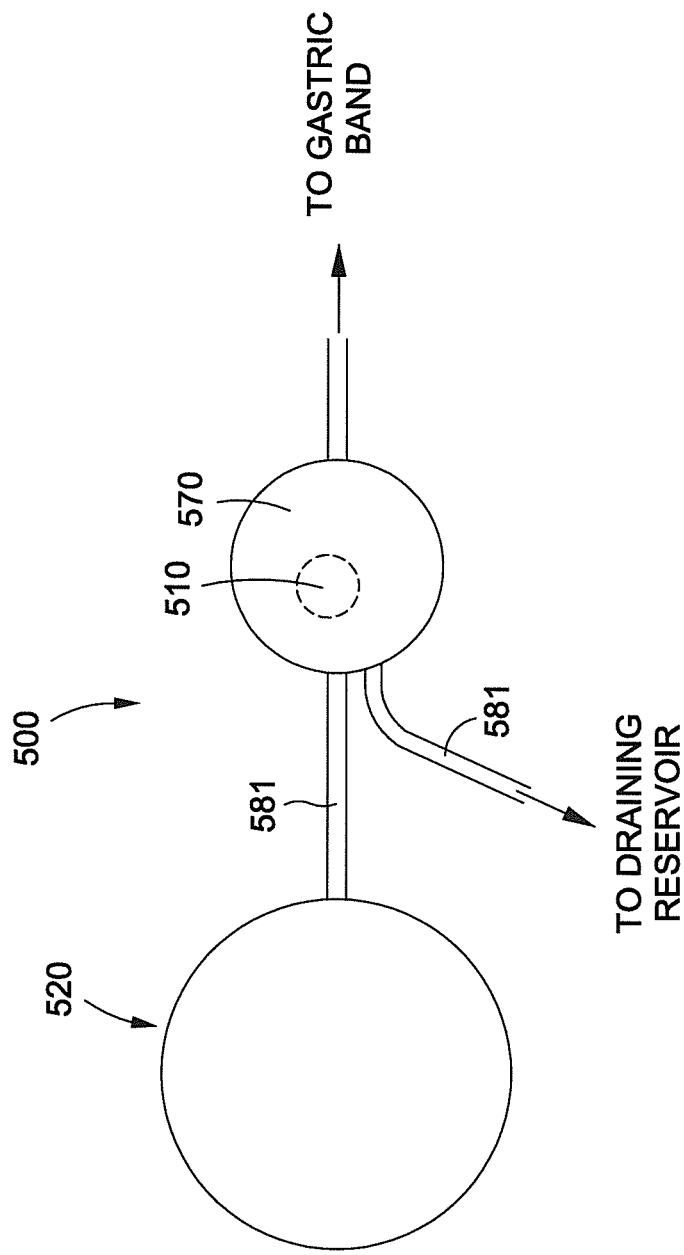
FIG. 5A illustrates a schematic representation of a gastric banding system according to an embodiment of the present invention.
Figure 5B:
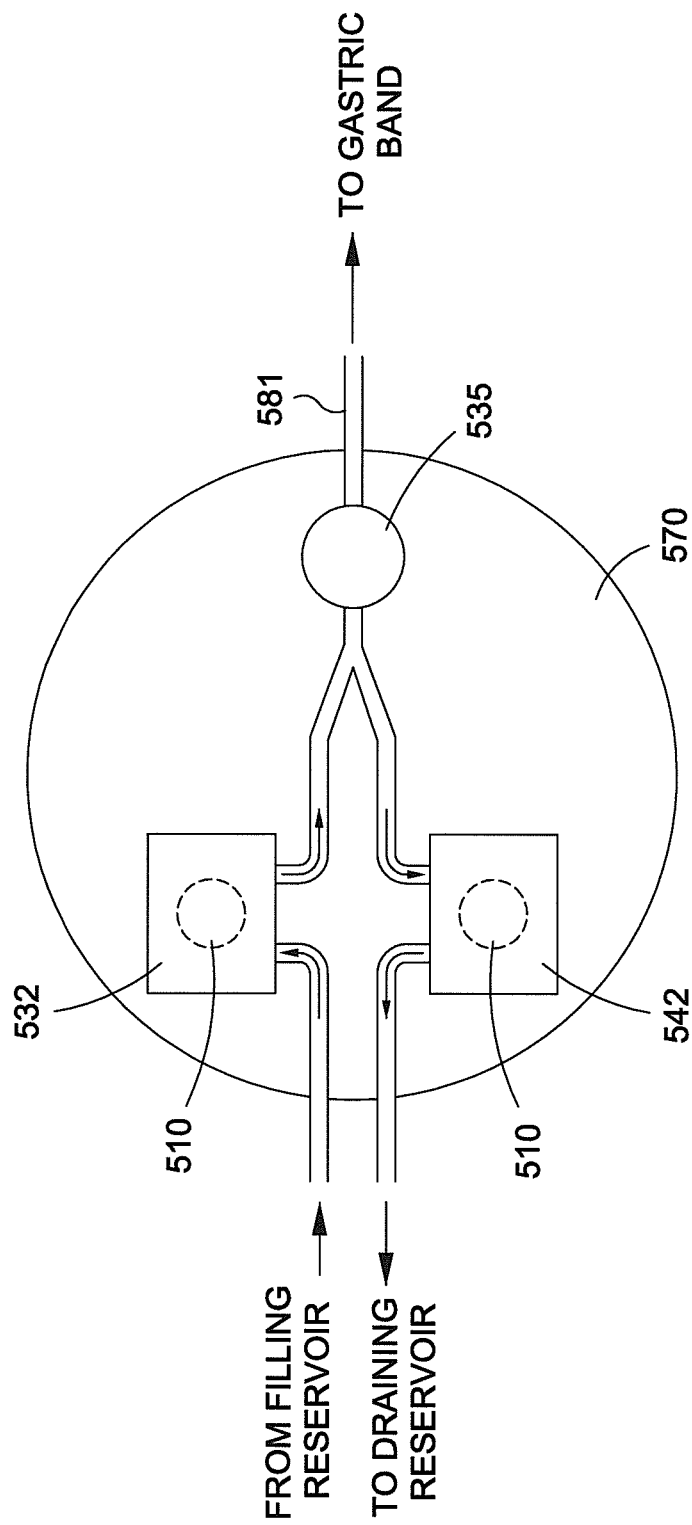
FIG. 5B illustrates a junction box with peristaltic pumps as represented in FIG. 5A according to an embodiment of the present invention.

In accordance with an embodiment, and with reference to FIGS. 4A-4B, the gastric banding system 400 comprises a chamber 422 that includes a filling reservoir 420, a piston 423, and a spring 410 that drives the piston 423 within the chamber 422. The chamber 422 also includes the draining reservoir 450 separated from the filling reservoir 420 by the piston 423. The filling valve 430, the draining valve 440, and the flow meter 435 are contained within the junction box 470 that is connected via a flexible tubing 481 to the gastric band.

As noted above, the chamber 422 is hermetically sealed to facilitate implantation in a patient's body. Because the chamber 422 is sealed, unless the filling valve 430 is open, the potential energy stored in the spring 410 is not discharged. When the filling valve 430 is open, the force created by the potential energy stored in the spring 410 is greater than the resistance of the gastric band to inflation. The spring 410 therefore releases an amount of the potential energy that causes the piston 423 to move within the chamber 422 and pump an amount of fluid from the filling reservoir 420 through the filling valve 430 and the flow meter 435 into the gastric band. When the flow meter 435 indicates a desired amount of fluid has moved into the gastric band, the filling valve 430 is closed and the piston 423 stops moving.

Because the chamber 422 is sealed, as the piston 423 moves to pump fluid out of the filling reservoir 420, a vacuum pressure is generated in the draining reservoir 450. When the draining valve 440 is opened, this vacuum pressure is at a lower pressure than the pressure that exists in the gastric band, so the fluid from the gastric band flows into the draining reservoir 450 until the pressures are equalized or until the valve 440 is closed. The valves 430 and 440 may be alternately opened and closed until substantially all the fluid from the filling reservoir 420 has moved through the gastric band into the draining reservoir 450. As noted above, a separate port may be utilized to re-fill the filling reservoir 420 and/or drain the draining reservoir 450.

In an embodiment, the fluid within the filling reservoir 420 may be housed within a pouch or other flexible enclosure. The piston 423 acts on the pouch to facilitate driving the fluid from the pouch into the gastric band. Utilizing a pouch to house the fluid reduces the need to seal the filling reservoir 420 from the draining reservoir 450. For example, where no pouch is utilized, the piston 423 needs to seal the filling reservoir 420 from the draining reservoir 450 to reduce undesired leakage of the fluid from the filling reservoir 420. Such sealing increases the friction between the chamber 422 and the piston 423 and therefore requires an increased force from the spring 410. Utilizing a pouch allows this friction to be reduced in order to minimize the amount of force provided by the spring 410. A similar pouch may also be utilized in the draining reservoir 450. Although these pouches are disclosed with respect to FIGS. 4A-4B, it should be understood that a similar pouch may be utilized in connection with the various other embodiments disclosed in or contemplated by this disclosure.

In accordance with an embodiment, the compression spring 410 may be replaced with another potential energy storage device. For example, the spring 410 may be located in the filling reservoir 420 and may be an extension spring to facilitate pumping fluid from the filling reservoir 420 into the gastric band.

Turning now to FIGS. 5A-5D, an embodiment of the gastric banding system 500 comprises a filling reservoir 520 coupled to a junction box 570 via a flexible tubing 581. The junction box 570 comprises the potential energy storage device 510 that facilitates moving the fluid from the filling reservoir 520 to an inflatable portion of a gastric band. The junction box 570 is also coupled to a draining reservoir to facilitate removing fluid from the inflatable portion of the gastric band.

The junction box 570 further comprises a filling peristaltic pump 532 coupled to the filling reservoir 520 and the flow meter 535, and a draining peristaltic pump 542 coupled to the draining reservoir 550 and the flow meter 535. The pumps 532 and 542 contain the potential energy storage device 510 that facilitates moving fluid between the filling reservoir 520, the gastric band and the draining reservoir 550. The pumps 532 and 542 are activated by a wireless signal from a remote transmitter as discussed above.

The filling peristaltic pump 532 (the draining peristaltic pump 542 includes similar components and functionality—only one pump is specifically discussed here for convenience) comprises a roller barrel 580 and a co-axial compression arc 584, between which the flexible tubing 581 is routed. The roller barrel 580 comprises rollers 582 configured to apply pressure to the flexible tubing 581 in order to move fluid through the tubing. For example, as the roller barrel 580 rotates clockwise, fluid moves into the filling peristaltic pump 532 at the bottom left corner and moves out of the filling peristaltic pump 532 at the bottom right corner. The rollers 582 provide a squeezing pressure on the flexible tubing 581, thereby pushing fluid through the tubing in order to draw the fluid from the filling reservoir 520 and move the fluid into the gastric band and/or to remove fluid from the gastric band into the draining reservoir 550.

In this embodiment, the potential energy storage device 510 is a spiral spring that causes the roller barrel 580 to rotate when the potential energy is released. This release of potential energy is triggered by an arresting mechanism 590. The arresting mechanism 590 comprises a locking, sliding bar 592 that is biased against the roller barrel 580 by a compression spring 594. In this position, the sliding bar 592 prevents the roller barrel 580 from rotating by abutting one of the rollers 582. When the roller barrel 580 is stationary, the potential energy stored in the spring 510 is not released.

To release the potential energy, an electromagnet 596 is activated, for example, by a telemetric signal generated by a remote transmitter. When the electromagnet 596 is activated, the sliding bar 592 is drawn towards the electromagnet 596, thereby allowing the roller barrel 580 to rotate in response to the potential energy that is released from the spring 510. When the flow meter 535 indicates that an appropriate amount of fluid has moved into or out of the gastric band, the electromagnet 596 is deactivated and the sliding bar 592 returns to prevent the roller barrel 180 from rotating.

The pump 532 further comprises a valve 583 that operates in conjunction with the arresting mechanism 590. For example, when the electromagnet 596 is activated, the valve 583 is opened to allow fluid to move through the pump 532. Similarly, when the electromagnet 596 is deactivated, the valve 583 is closed to prevent excess fluid from exiting the pump 532.

Figure 6:
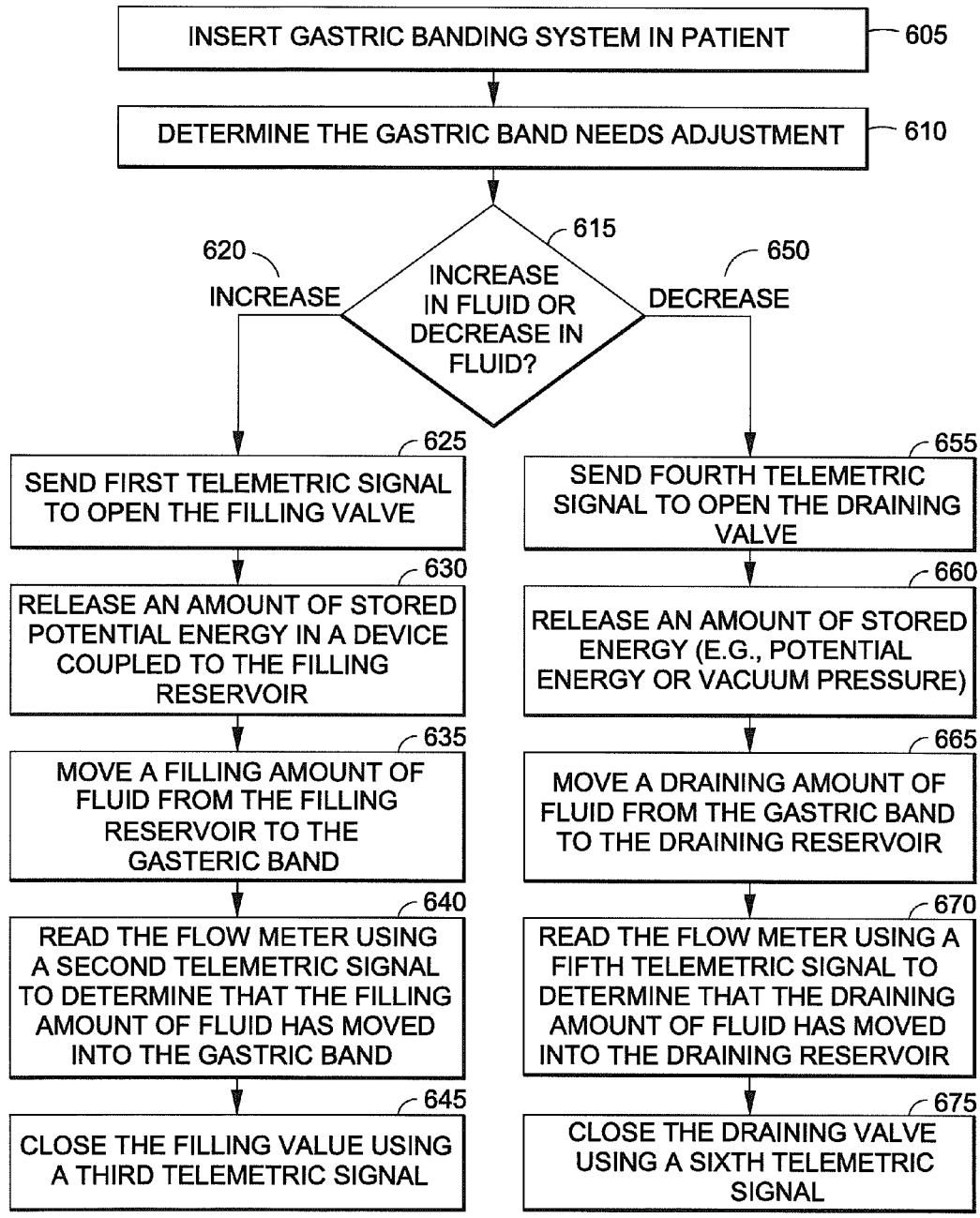
FIG. 6 is a flowchart illustrating an example method of using a gastric banding system according to an embodiment of the present invention.

Turning now to FIG. 6 (with reference to the gastric banding system 200 in FIG. 2), a method for operating the gastric banding system 200, according to an embodiment, is now disclosed. At step 605, the gastric banding system 200 is implanted in a patient. At some point, a physician determines that the gastric band 205 needs to be adjusted (step 610), and whether or not the gastric band 205 needs to be inflated or deflated (Step 615).

If the gastric band 205 needs to be inflated with an increase in the fluid in the gastric band 205 (step 620), the remote transmitter 260 is utilized to send a first telemetric signal to open the filling valve 230 (step 625). Opening the filling valve 230 allows an amount of stored potential energy in the potential energy storage device 210 to be released (step 630), and the amount of the stored potential energy causes fluid to move from the filling reservoir 220 to the gastric band 205 (step 635). The remote transmitter 260 is then utilized to read the flow meter 235 using a second telemetric signal to determine that an appropriate amount of fluid has entered the gastric band 205 (step 640). When the gastric band 205 is sufficiently inflated, a third telemetric signal is transmitted from the remote transmitter 260 in order to close the filling valve 230 (step 645).

If the gastric band 205 needs to be deflated with a decrease in the fluid in the gastric band 205 (step 650), the remote transmitter 260 is utilized to send a fourth telemetric signal to open the draining valve 240 (step 655). Opening the draining valve 240 allows an amount of stored energy (e.g., in the form of potential energy and/or vacuum pressure) to be utilized (step 660), to move an amount of fluid from the gastric band 205 to the draining reservoir 250 (step 665). The remote transmitter 260 is then utilized to read the flow meter 245 using a fifth telemetric signal to determine that an appropriate amount of fluid has been removed from the gastric band 205 (step 670). When the gastric band 205 is sufficiently deflated, a sixth telemetric signal is transmitted from the remote transmitter 260 in order to close the draining valve 240 (step 675).

As long as the stored potential energy remains in the gastric banding system 205, the above process may be repeated as often as the physician deems necessary to appropriately adjust the gastric band 205. Additionally, such adjustments may be made without invasive injections utilized in existing gastric banding systems. Furthermore, such adjustments may be made with reduced power output from the remote transmitter 260 when compared with existing gastric banding systems that drive the implanted pumps with inductive power.

It should be understood that "first telemetric signal," "second telemetric signal," etc. are used to distinguish between different communications with remote transmitter 260. These different communications may nonetheless all be on the same or different frequencies and may emanate from the same or different antennas. Further, the telemetric signals may be a continuous signal, and different time periods of the continuous signal may be referred to as the "first," "second," etc. telemetric signal.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. An implantable device that uses potential energy to facilitate the movement of fluid to an inflatable portion of a gastric band, the implantable device comprising:
   a filling reservoir for holding the fluid;
   a first device operatively coupled to the filling reservoir, wherein the first device comprises stored potential energy that facilitates moving an amount of the fluid to the inflatable portion of the gastric band; and
   a filling valve coupled between the filling reservoir and the gastric band, the filling valve being open or closed based on a first telemetric signal received from a remote transmitter, and when the filling valve is open, a portion of the stored potential energy is released causing the amount of the fluid to move from the filling reservoir into the inflatable portion of the gastric band, and when the filling valve is closed, a remaining amount of the stored potential energy remains stored in the first device, wherein the implantable device further comprises:
   a draining reservoir; and
   a draining valve coupled between the draining reservoir and the gastric band, the draining valve being open or closed based on a second telemetric signal received from the remote transmitter, and when the draining valve is open, a portion of the fluid in the inflatable portion of the gastric band moves into the draining reservoir, and wherein the implantable device further comprises:
   a sealed chamber that includes the filling reservoir and the draining reservoir; and
   a piston disposed between the filling reservoir and the draining reservoir and between a filling end of the sealed chamber and a draining end of the sealed chamber, wherein the filling valve is coupled to the filling end and the draining valve is coupled to the draining end, wherein the piston moves toward the filling end of the sealed chamber in response to the portion of the stored potential energy being released, and wherein the volume of the filling reservoir and the volume of the draining reservoir change as the piston moves in the sealed chamber.

2. The implantable device of claim 1, wherein a vacuum pressure is generated in the draining reservoir in response to the piston moving toward the filling end of the sealed chamber, and wherein the vacuum pressure causes a draining amount of the fluid to be removed from the gastric band when the draining valve is open, wherein the draining amount of the fluid moves into the draining reservoir from the gastric band.

3. An implantable device that uses potential energy to facilitate the movement of fluid to an inflatable portion of a gastric band, the implantable device comprising:
   a filling reservoir for holding the fluid, wherein a volume of the filling reservoir is approximately 10 mL;
   a spring operatively coupled to the filling reservoir, wherein the spring comprises stored potential energy that facilitates moving an amount of the fluid to the inflatable portion of the gastric band;
   a filling valve coupled between the filling reservoir and the gastric band, the filling valve being open or closed based on a first telemetric signal received from a remote transmitter, and when the filling valve is open, a portion of the stored potential energy is released causing the amount of the fluid to move from the filling reservoir into the inflatable portion of the gastric band, and when the filling valve is closed, a remaining amount of the stored potential energy remains stored in the spring;
   a draining reservoir;
   a draining valve coupled between the draining reservoir and the gastric band, the draining valve being open or closed based on a second telemetric signal received from the remote transmitter, and when the draining valve is open, a portion of the fluid in the inflatable portion of the gastric band moves into the draining reservoir;
   a flow meter for determining the amount of the fluid moving into or out of the inflatable portion of the gastric band;
   a junction box comprising the filling valve, the draining valve, and the flow meter;
      a hermetically sealed chamber that includes the filling reservoir and the draining reservoir; and
      a piston disposed between the filling reservoir and the draining reservoir and between a filling end of the hermetically sealed chamber and a draining end of the hermetically sealed chamber, wherein the spring is coupled to the piston, wherein the filling valve is coupled to the filling end and the draining valve is coupled to the draining end, wherein the piston moves toward the filling end of the hermetically sealed chamber in response to the portion of the stored potential energy being released, and wherein the volume of the filling reservoir and the volume of the draining reservoir change as the piston moves in the hermetically sealed chamber.

4. The implantable device of claim 3, wherein the filling valve and the draining valve are selected from a group consisting of a piezoelectric valve, a solenoid valve, and combinations thereof.

5. The implantable device of claim 3, wherein the filling valve and the draining valve are powered by inductive powering signals received from the remote transmitter.

6. The implantable device of claim 3, further comprising a pouch disposed within the filling reservoir, wherein the fluid is disposed within the pouch.

7. The implantable device of claim 3, wherein a vacuum pressure is generated in the draining reservoir in response to the piston moving toward the filling end of the hermetically sealed chamber, and wherein the vacuum pressure causes a draining amount of the fluid to be removed from the gastric band when the draining valve is open, wherein the draining amount of the fluid moves into the draining reservoir from the gastric band.

* * * * *